United States Patent [19]

Meilland

[11] Patent Number: Plant 5,956

[45] Date of Patent: Apr. 28, 1987

[54] ROSE PLANT—MEIPOQUE VARIETY

[75] Inventor: Marie-Louise Meilland, Antibes, France

[73] Assignee: The Conard-Pyle Company, West Grove, Pa.

[21] Appl. No.: 763,997

[22] Filed: Aug. 9, 1985

[51] Int. Cl.[4] ..... A01H 5/00

[52] U.S. Cl. ..... Plt./1

[58] Field of Search ..... Plt./1

*Primary Examiner*—James R. Feyrer

*Attorney, Agent, or Firm*—Burns, Doane, Swecker & Mathis

[57] ABSTRACT

A new and distinct variety of shrub rose plant is provided which forms in abundance single rose-carmine flowers of five petals having a white center. The new variety has a vigorous growth habit and is well-adapted for growing in the landscape where it reflowers well all season long. Attractive red fruits commonly are present on the new variety during the autumn-winter.

13 Drawing Figures

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) of the new variety was the variety Meituraphar which is marketed in Europe under the trademark of Anne De Bretagne. The male parent (i.e., the pollen parent) of the new variety was the variety Meirisouru which is marketed in Europe under the trademark of Nirvana. The parents of the new variety are non-patented in the United States. The parentage of the new variety can be summarized as follows:

Meituraphar × Meirisouru

The seeds resulting from the above pollination were sown and 170 plantlets were obtained which were physically and biologically different from each other. Selective study resulted in the identification of a single plant of the new variety.

It was found that the new variety of shrub rose plant of the present invention possesses the following combination of characteristics:

(a) forms in abundance over an extended period of time attractive rose-carmine single flower blossoms of five petals having a white center, (b) forms in the fall attractive red fruits, (c) exhibits a vigorous growth habit, (d) is hardy and relatively disease-resistant, and (e) is particularly well-suited for growing in the landscape.

The new variety meets the needs of the horticultural industry for virtually all uses. Since the new variety reflowers well without stopping all season long and the attractive red fruit which is formed in the fall imparts an added decorative effect, the new variety is particularly well-suited for growing in landscape situations. The exceptional vigor, floriferousness, and hardiness of the new variety are noteworthy.

The new variety has been found to undergo asexual propagation by a number of routes, including budding and grafting. The characteristics of the new variety have been found to be strictly transmissible by such asexual propagation from one generation to another.

The new variety has been named the Meipoque variety.

BRIEF DESCRIPTION OF THE PHOTOGRAPH

The accompanying photograph shows, as nearly true as it is reasonably possible to make the same, in a color illustration of this character, typical specimens of plant parts of the new variety. The rose plants of the new variety described herein were grown at LeLuc, France.

DETAILED DESCRIPTION

Figures 1, 2, 3, 4, 5, 6, 7, 8, 9, 10, 11, 12, 13:
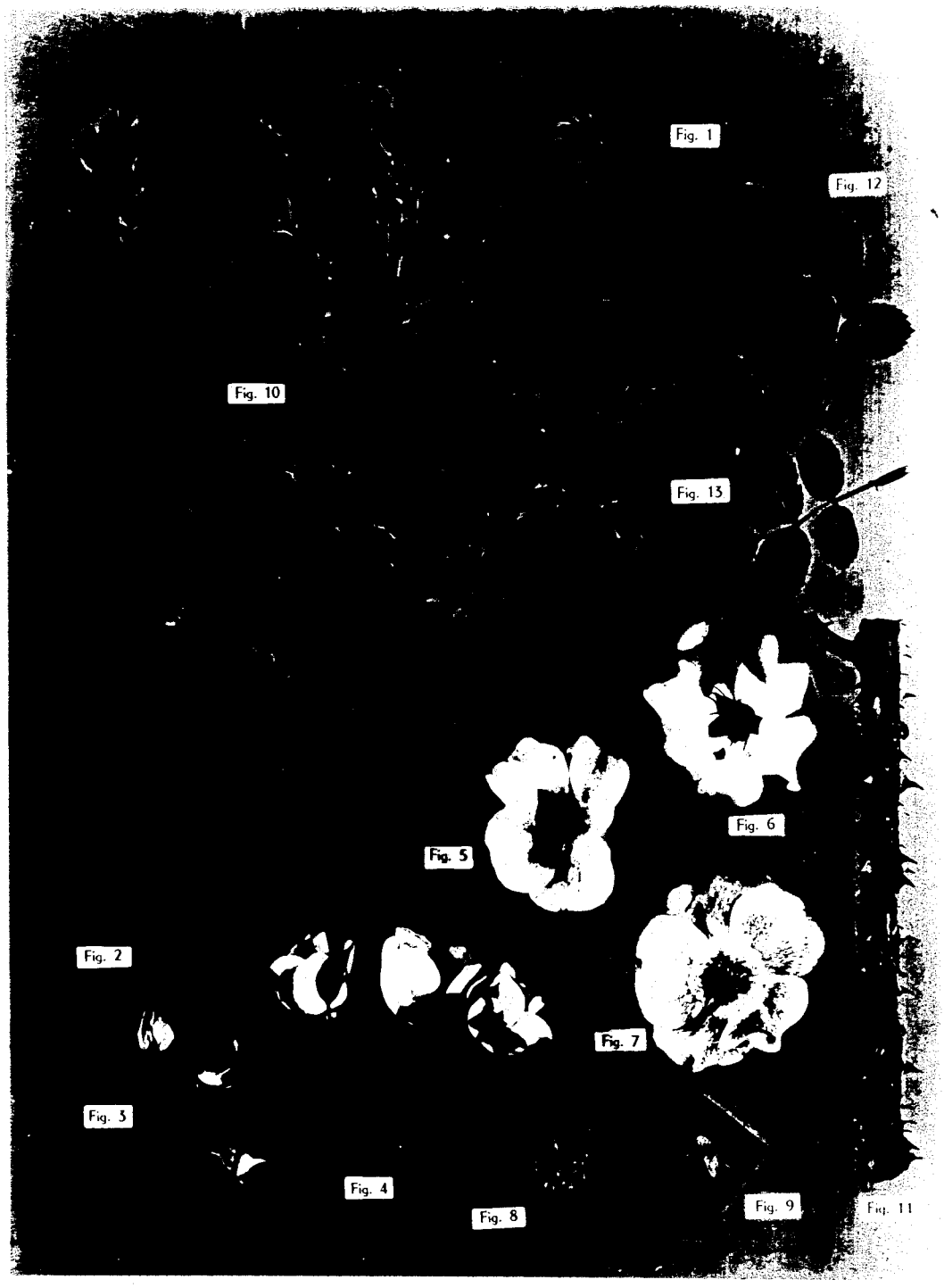
FIG. 1 illustrates a specimen of a young shoot.
FIG. 2 illustrates a specimen of several flowering buds before the opening of the sepals.
FIG. 3 illustrates a specimen of three flowering buds at the opening of the sepals.
FIG. 4 illustrates a specimen of three flowers in the course of opening.
FIG. 5 illustrates a specimen of an open flower — plan view—obverse.
FIG. 6 illustrates a specimen of an open flower — plan view—reverse.
FIG. 7 illustrates a specimen of a fully open flower — plan view—obverse.
FIG. 8 illustrates a specimen of a floral receptacle showing the arrangement of the stamens.
FIG. 9 illustrates a specimen of a floral receptacle showing the arrangement of the pistils (stamens removed)
FIG. 10 illustrates a specimen of a flowering stem showing a typical cluster of buds.
FIG. 11 illustrates a specimen of a main branch.
FIG. 12 illustrates a specimen of a leaf with three leaflets — upper surface.
FIG. 13 illustrates a specimen of a leaf with five leaflets — under surface.

The chart used in the identification of colors is that of The Royal Horticultural Society (R.H.S. Colour Chart). The terminology preceding the numbered references has been added to designate in common terms the corresponding colors. The description is based on one-year old specimens of the new variety during July while budded on *Rosa froebelii* understock and grown in a nursery at LeLuc, France.

Class: Shrub.

Plant:

*Height.*—Approximately 1.5 meters.

*Habit.*—Arching and semi-erect.

Branches:

*Color.*—Young stems: reddish. Adult Wood: Yellow-Green Group 146D.

Leaves:

*Petioles.*—Upper surface: grooved, reddish-brown on young foliage, medium brown on adult foliage. Under surface: light green with glandular sides.

*Leaflets.*—Number: 3, 5 (most often), and sometimes 7. At times the first pair of leaflets is not complete. Shape: oval with assymetric base. Serration: regularly serrate. Texture: leathery. General appearance: relatively small foliage which is dense and semi-glossy. Color (young foliage): Upper surface: reddish-brown. Under surface: reddish-brown. Color (adult foliage): Upper surface: bronze green, Green Group 139A. Under surface: medium green, Yellow-Green Group 146B.

Inflorescence:

*Number of flowers.*—Numerous flowers per floral stem commonly numbering 5 to 35 per floral stem.

*Peduncle.*—Its length is approximately 4 cm on average.

*Buds.*—Shape: conical. Length: approximately 2 cm on average. Color: Red Group 46B on cream upon opening.

*Flower.*—Form: single and flat when fully open. Diameter: approximately 8 cm on average. Color (when opening begins): Upper surface: Red Group 46C on cream. Under surface: Red Group 50A breaking down irregularly to Red Group 50C. Color (when partially open): Upper surface: Red Group 52A with a large whitish base. Under surface: whitish and suffused with Red Group 52B to 52D. Color (at end of opening): Upper surface: Red Group 52C passing to Red Group 52D with a whitish base. Under surface: whitish and suffused with Red Group 52A passing to Red Group 52D. The suffusion has a tendency to blue. Fragrance: none. Lasting quality: average. Petal form: fan shaped, often with a depression at the center of the outer margin. Petal number: 5. Stamen number: approximately 82 on average. Anthers: yellow with an ochre margin. Pistils: approximately 30 on average.

Development:

*Vegetation.*—Vigorous.

*Blossoming.*—Continuous throughout season.

*Hardiness.*—Good.

*Disease resistance.*—Good.

I claim:

1. A new and distinct variety of shrub rose plant characterized by the following combination of characteristics:

(a) forms in abundance over an extended period of time attractive rose-carmine single flower blossoms of five petals having a white center, (b) forms in the fall attractive red fruits, (c) exhibits a vigorous growth habit, (d) is hardy and relatively disease resistant, and (e) is particularly well-suited for growing in the landscape;

substantially as herein shown and described.

* * * * *